(12) United States Patent
Triel et al.

(10) Patent No.: US 9,084,867 B2
(45) Date of Patent: Jul. 21, 2015

(54) INJECTION MOULDING CATHETER

(75) Inventors: Egon Triel, Gilleleje (DK); Johnny Wagner, Zhuhai (CN)

(73) Assignee: Coloplast A/S, Humlebaek (DK)

( * ) Notice: Subject to any disclaimer, the term of this patent is extended or adjusted under 35 U.S.C. 154(b) by 697 days.

(21) Appl. No.: 13/378,603

(22) PCT Filed: Jun. 25, 2010

(86) PCT No.: PCT/DK2010/050166
§ 371 (c)(1),
(2), (4) Date: Feb. 20, 2012

(87) PCT Pub. No.: WO2010/149175
PCT Pub. Date: Dec. 29, 2010

(65) Prior Publication Data
US 2012/0150130 A1    Jun. 14, 2012

(30) Foreign Application Priority Data

Jun. 26, 2009    (DK) ................................ 2009 70041

(51) Int. Cl.
*B29C 45/26* (2006.01)
*A61M 25/00* (2006.01)
*B29C 45/36* (2006.01)
*B29L 31/00* (2006.01)

(52) U.S. Cl.
CPC ............ *A61M 25/0015* (2013.01); *B29C 45/36* (2013.01); *A61M 25/0017* (2013.01); *B29C 45/261* (2013.01); *B29C 45/2628* (2013.01); *B29C 2045/366* (2013.01); *B29L 2031/7542* (2013.01)

(58) Field of Classification Search
CPC .................. B29C 2045/363; B29C 2045/366; B29C 45/261; B29C 45/2628; B29C 45/36; B29L 2031/7542
USPC ................... 264/328.1, 334; 425/577; 249/64
See application file for complete search history.

(56) References Cited

U.S. PATENT DOCUMENTS

| 2,855,929 | A |   | 10/1958 | Hein, Jr. |
| 2,972,779 | A |   | 2/1961  | Cowley |
| 3,737,272 | A | * | 6/1973  | Segmuller ...................... 425/595 |
| 3,830,236 | A |   | 8/1974  | Hanke |
| 3,901,965 | A |   | 8/1975  | Honeyman |

(Continued)

FOREIGN PATENT DOCUMENTS

| FR | 2817793 | 6/2002 |
| GB | 1580924 | 12/1980 |

(Continued)

*Primary Examiner* — Jill Heitbrink
(74) *Attorney, Agent, or Firm* — Coloplast Corp., Coloplast A/S; Nick Baumann

(57) ABSTRACT

A method of injection molding a catheter assembly, the method comprising providing a mold having an elongated cavity in the form of an external surface of the catheter assembly, providing a core pin in the longitudinal axis of the catheter assembly inside the cavity in the form of an inner lumen of the catheter assembly, where the core pin has a distal end that is fixed in place and a proximal free end, providing a first and a second molding member where each one of the first and the second molding members has a fixed end and a free end, in a radial direction of the elongated cavity, preparing the mold by arranging the free ends of the two molding members to support the core pin, injecting a liquid catheter material into the mold, letting the liquid material solidify.

12 Claims, 3 Drawing Sheets

(56) References Cited

U.S. PATENT DOCUMENTS

| | | | |
|---|---|---|---|
| 4,970,926 A * | 11/1990 | Ghajar et al. | 83/468.94 |
| 5,104,606 A * | 4/1992 | Donoghue | 264/328.1 |
| 5,240,397 A * | 8/1993 | Fay et al. | 425/145 |
| 5,919,170 A | 7/1999 | Woessner | |
| 7,429,348 B2 * | 9/2008 | Soerensen | 264/328.1 |
| 7,794,644 B2 * | 9/2010 | Taylor et al. | 264/328.12 |
| 2005/0033237 A1 | 2/2005 | Fentress et al. | |
| 2005/0104255 A1 * | 5/2005 | Mejlhede et al. | 264/328.1 |
| 2005/0192560 A1 | 9/2005 | Walls et al. | |
| 2008/0179792 A1 | 7/2008 | Kurimoto et al. | |

FOREIGN PATENT DOCUMENTS

| | | |
|---|---|---|
| GB | 2230702 | 10/1990 |
| WO | 03002325 | 1/2003 |
| WO | 2005046959 | 5/2005 |
| WO | 2008155145 | 12/2008 |

* cited by examiner

100
INJECTION MOULDING CATHETER

FIELD OF THE INVENTION

A method of injection moulding a catheter assembly comprising a catheter tube having a proximal end and a distal end, an insertable tip closing the proximal end of the catheter tube and at least two drainage eyes arranged on the side walls of the catheter tube.

BACKGROUND OF THE INVENTION

The production methods of medical catheters, especially urinary catheters, have been seen as complex processes where the intermediate products are subject to a number of different production steps before being ready for packaging, shipping and for the use by the consumer.

Urinary catheters usually comprise a number of technical features which characterize the catheters. These features are: a catheter tube, a catheter tip, drainage eyes and a connector. Each one of these technical features usually require its distinctive production step in order to make the feature a part of the finished catheter.

An example of these distinctive production steps may be seen in the production of a well known type of intermittent catheter, such as the Easicath catheter by Coloplast A/S or the LoFric catheter by Astratech AB. The catheter tube is extruded in a thermoplastic material, having a predetermined diameter and a predetermined length which vary on basis of the user groups these catheters are supposed to serve. Subsequently, the insertable proximal end of the catheter tube is provided with an insertable tip which closes the proximal end of the catheter tube and provides an low impact tip which reduces the risk of causing damage to the mucosa of the urinary channel during the insertion of the catheter. After the tipping of the catheter, one or more drainage eyes are provided on the side walls of the tubing close to the proximal end of the catheter tube in order to provide drainage from the urine bladder subsequent to the insertion of the catheter. Finally, a connector is attached to the distal end of the catheter tube to provide a structure for allowing the user to grip and control the catheter during insertion and retraction and also to provide a connector for a urine bag if necessary. This type of catheter may, subsequently to the aforementioned production steps, be subjected to further production steps in order provide surface treatment, sterilization, etc.

This method of producing a catheter may be seen as time consuming, complex and costly as the catheter is subjected to a number of different production steps, where each step requires different resources, such as a specific machine, man hours for operating the machine or machine time for providing the technical feature. And if any one of these production steps fails, the resulting catheter has to be discarded.

WO 2005/046959 discloses a method for the injection moulding of soft needle catheters comprising a hub and a soft flexible part. The disclosed method provides a catheter that is designed to be provided as a sleeve surrounding an intravenous injection needle, which means that the proximal end of the catheter is open for the insertion of an IV injection needle along its longitudinal axis.

US 2005/033237 discloses a method for injection moulding intravenous needle catheters having a catheter tube and a hub, where the catheter tube is open in its proximal end so that an intravenous injection needle may protrude through the proximal end of the catheter.

Previously, the injection moulding of a catheter assembly has been affected by the fact that the core pin, which forms the inner lumen of the catheter tube, has been stabilized by anchoring the free end of the core pin on the outside the injection moulding cavity. This means that the free end of the core pin extends outside the elongated cavity into an anchoring mechanism that is located past the mould, so that the pin will maintain its stability during the injection of the liquid catheter material into the mould. Thus, catheters which are moulded in such a way have an open tip. Such catheters are commonly used for intravenous applications, where the catheter surrounds a syringe needle and where the syringe needle is removed subsequent to the insertion of the needle and the catheter. However, such a method is not well suited for the moulding of urinary catheters and the use of this method would mean that subsequent to the solidification of the catheter material, and subsequent to the removal of the catheter from the mould, the tip has to be formed. Hence there is a need for an improved method of injection moulding catheters which have a tip that closes off the insertable end of the catheter tube.

SUMMARY OF THE INVENTION

According to the invention there is provided a method of injection moulding a catheter assembly comprising a catheter tube having a proximal end and a distal end, an insertable tip closing off the proximal end of the catheter tube and at least two drainage eyes arranged on the side walls of the catheter tube, the method comprising: providing a mould having an elongated cavity having a longitudinal axis and having a cylindrical shape defining an external surface of the catheter assembly, providing a core pin inside the cavity in the longitudinal axis of elongated cavity, where the core pin is in the form of an inner lumen of the catheter assembly, where the core pin has a distal end that is fixed in place and a proximal free end, providing a first and a second moulding member where each one of the first and the second moulding members has a fixed end and a free end, in a radial direction in relation to the longitudinal axis of the elongated cavity, preparing the mould by arranging the free ends of the two moulding members to support the core pin, injecting a liquid catheter material into the mould, letting the liquid material solidify, withdrawing the two moulding members from the core pin in a radial direction away from the core pin, and removing the catheter assembly from the mould.

By providing a method of injection moulding a catheter according to the present invention, the two moulding members are provided inside the cavity in order to secure, fix or stabilize the core pin which forms the inner lumen of the catheter. The core pin may be seen as a cylindrical pin, which extends longitudinally inside the elongated cavity. The first and the second moulding members provide a support in a radial direction, so that the free end of the core pin is prevented from being displaced during the high pressure injection of the liquid catheter material into the mould. This means that the free end of the core pin does not need to extend through the cavity for anchoring and the mould may be formed in such a way that the tip of the catheter is moulded at the same time as the rest of the catheter assembly and the tip is fully integral with the catheter tube.

Within the meaning of the present invention the longitudinal axis of the catheter tube is defined as an axis that extends along the radial centre of the catheter tube as seen on an unbent or undistorted catheter tube. The terms proximal and distal directions may be seen as in view of the user during insertion, i.e. the proximal end is the end closest to the user and the distal end faces away from the user. Furthermore, the term radial, radial axis or radial direction may be seen as a direction that is perpendicular to and intersects the longitudinal axis of the catheter tube.

In one embodiment of the present invention, the first and the second moulding members may be positioned on opposite sides of the elongated cavity. This means that the first moulding member may prevent the core pin from displacing in the radial direction that corresponds to the radial direction of the first moulding member and the second moulding member may prevent the core pin from displacing in the opposite direction.

Furthermore, the free ends of the first and the second moulding members may be formed to the curvature of the core pin, so that when the moulding member abuts the core pin, the surface area of the free end of the moulding member mates with the corresponding surface area of the core pin so that the free end not only prevents displacement in the radial direction of the moulding member but also in any radial direction that is perpendicular to the surface area covered by the free end.

Alternatively, the core pin may be provided with surface depressions in the form of slots or sockets which mate with the free ends of the first and the second moulding members, which fit into the slots or sockets, so that the free end not only prevents displacement in the radial direction of the moulding member but also in any radial direction that is in a range from approximately ±90° in respects of the radial direction of the moulding member.

In one embodiment of the present invention, the first and the second moulding members may be positioned in an area that is proximal to approximately 50% of the length of the core pin, such as 70% of the length of the core pin, such as 80% of the length of the core pin, such as 90% of the length of the core pin. Hence, the moulding members may be positioned closer to the proximal end than the distal end of the core pin. The proximal free end of the core pin is the part of the core pin which is most likely to be displaced during the high pressure injection of the liquid catheter material into the elongated cavity, as the movement of liquid catheter material may push or press the free end of the core pin from its longitudinal axis. By positioning the moulding members closer to the proximal free end than its fixed distal end, it is possible to minimize the displacement of the free end of the core pin. Further, by moving the moulding members closer and closer to the proximal free end of the core pin it is possible to decrease the risk of displacement of the free end during the injection.

In one embodiment of the present invention, the first moulding member may be positioned inside the elongated cavity at a first longitudinal position and the second moulding member may be positioned inside the elongated cavity at a second longitudinal position that is different from the first longitudinal position. The first moulding member may be positioned close to the proximal free end of the core pin while the second moulding member may be positioned at a position that is proximal to or distal to the longitudinal position of the first moulding member. By positioning the first and the second moulding members at different positions, the moulding members provide support to a greater longitudinal area of the core pin than if they would be positioned directly opposite each other. One of the moulding members could be positioned to support the free end of the core pin, while the other could be positioned to support a central longitudinal area of the core pin, in order to prevent both the central longitudinal area and the free end from being displaced during the high pressure injection of the liquid catheter material.

In one embodiment of the present invention, the first and the second moulding members may be provided having a shape that defines the drainage eyes arranged in side walls of the catheter tube. In alternative embodiments of the present invention and/or during the manufacturing of conventional urinary catheters, drainage eyes may be cut into the catheter tubes, subsequent to the manufacturing of catheter tubes, using a cutting tool where a section of the side wall of the catheter tube is cut and removed in order to provide a drainage eye in the form of a through-going opening. By providing the first and second moulding members in the form of drainage eyes, the drainage eyes of the catheter may be provided during the injection moulding of the catheter tube of the catheter assembly and the catheter assembly would not require a further process step to provide the through-going opening.

In one embodiment of the present invention, the drainage eyes may be cut into the catheter tube after the injection moulding of the catheter assembly.

In one embodiment of the present invention, each one of the at least two drainage eyes of the catheter assembly may have an outer edge that is rounded. The drainage eyes of catheters that have been cut to provide a through-going opening usually have an outer edge that may be seen as being relatively sharp, i.e. an edge that may cause discomfort or trauma to the urethra during the insertion of the catheter. By providing the outer edge with a rounded edge, it may be possible to minimize the discomfort or the trauma to the urethra during insertion.

In one embodiment of the present invention, the free ends of the first and the second moulding members provided may have such a shape that the outer edge of the at least two drainage holes may be rounded during the injection moulding. Thus, the provision of the drainage eyes during the injection moulding using the first and the second moulding members may be modified so that the form of an outer periphery of the moulding members corresponds to a rounded outer edge of the drainage eye. This means that the free end of the moulding member may have a first circumference that is smaller than a second circumference of the fixed end of the moulding member. The transition between the first circumference and the second circumference may be in the form of the rounded edge, i.e. the corresponding form for moulding the rounded edge of the drainage eye. Such a form may for example be a concave surface area, a linear surface area or any surface area that may form a rounded edge.

The outer edge may also be rounded subsequent to the removal of the catheter assembly from the mould. The use of moveable moulding members for the forming of the drainage eyes may cause wear and tear to the catheter assembly mould or to the moulding members. The wear and tear can have the consequence that the area where the moulding member joins the cavity may not be as tight as desired and this lack of tightness can lead to a small gap between the two surfaces. Such a gap causes a defect in the moulded article, in the form of an unwanted protrusion or a fin. Such a protrusion or fin will occur on the outer edge of the drainage eye, which means that the drainage eye may have a defect that may be seen as unfortunate for the user of the catheter. Thus, by rounding the eye subsequent to the withdrawal of the catheter assembly from the mould, the protrusion or the fin may be rounded off prior to the intended use of the catheter assembly.

In one embodiment of the present invention, the mould may be provided comprising a first half and a second half that mate each other longitudinally or vertically and define the mould cavity when assembled and separate longitudinally or vertically to expose the cavity. This means that the catheter assembly mould can be separated upon solidification of the catheter material and the moulded catheter assembly may be ejected from the catheter mould using conventional methods, such as by ejecting the catheter assembly using an ejector pin.

By using such a mould, the catheter assembly may be provided with a number of different structures, which protrude in a radial direction away from the outer surface of the catheter tube, in case there is a practical requirement for such structures.

During the manufacturing process of the catheter assembly, wear and tear may occur to the first and the second halves, which might result in the joint between the halves becoming weak and it may result in a protrusion or a fin running along the catheter tube. Such a protrusion or fin may be seen as a defect on the catheter tube and the fin might cause discomfort or damage to the urethra of the user during insertion.

Thus, in one embodiment of the present invention, the mould provided may be a single piece mould having an elongated cavity, where the elongated cavity may be in the form of the external surface of the catheter assembly and the catheter assembly may be removed from the mould by a withdrawal along the longitudinal axis of the catheter assembly. By providing a one-piece mould, it is possible to prevent the occurrence of fins or protrusion on the catheter tube caused by joint lines, as the mould is a one-piece mould and there is no joint between the first and the second half. Thus, in order to remove the catheter assembly from the mould, the core pin is removed from the mould without removing the core pin from the catheter assembly. That is, the movement of the core pin removes the catheter assembly from the mould. In order to perform this, it is necessary that the frictional forces between the core pin and the catheter assembly is higher than the frictional forces between the catheter assembly and the mould cavity.

The use of a single piece mould means that the part of the catheter assembly moulded using the single piece mould cannot have any protrusions or structures that protrude in a radial direction away from the surface of the catheter tube, as such protrusions would maintain the catheter assembly within the mould and increase the forces required to remove the catheter from the mould considerably.

In one embodiment of the present invention, the mould provided may comprise a proximal single piece mould having an elongated cavity, where the elongated cavity in the form of the external surface of the catheter tube, catheter tip, and distally, a first half and a second half that mate longitudinally or vertically to each other and define the mould cavity of the catheter connector when assembled and separate longitudinally or vertically to expose the cavity. By providing a catheter assembly mould with two types of moulds, a one-piece mould for the catheter tube and a two piece mould for any structures that may not be moulded using the one-piece mould, it is possible to injection mould a catheter assembly that has complex structures extending in a radial direction away from the surface area of the catheter tube at the catheter assembly's distal end.

In one embodiment of the present invention, the catheter assembly may further comprise a connector at the distal end of the catheter tube. A catheter connector may be of such a complex structure that if the other parts of the catheter assembly are moulded using a single piece mould the catheter connector would most likely have to be added to the catheter assembly subsequent to the moulding of the remaining catheter assembly.

However, in one embodiment of the present invention, the mould provided may further comprise a cavity defining a connector and the connector is injection moulded simultaneously with the catheter assembly. This means that the catheter connector may be moulded in the same injection cycle as the rest of the catheter assembly. The connector may be shaped in such a way that it is suited for injection moulding in a one-piece mould, where it is ensured that there are no structures on the connector or the remaining part of the catheter assembly that make a withdrawal from the one-piece mould difficult, i.e. where the connector does not have any radial protrusions that might prevent the withdrawal.

Another method of providing a connector in the same injection cycle is by moulding the catheter using a one-piece mould and a mould having two halves, as mentioned above, where the mould having two halves is used to mould the connector and the one-piece mould is used to mould the catheter tube. This means that the shape or the design of the connector may have radial structures, such as ribs or protrusions which would prevent the use of the one-piece mould for the connector and such a connector may be moulded along with the remaining parts of the catheter assembly. One of the advantages of using a combination of a one-piece mould and a mould having two halves is that the insertable part of the catheter is formed using the one-piece mould, and any defects that might occur using the mould having two pieces would not affect the insertable part of the catheter assembly and thus would not cause any discomfort or trauma to the urethra of the user.

In another embodiment of the present invention, the connector may be provided in the injection mould prior to the injection moulding of the catheter assembly. This means that prior to the injection moulding of the catheter assembly an existing connector is positioned inside the cavity, and the injection moulding process would fuse the connector to the remaining catheter assembly during the injection moulding process. The connector may for example be placed at the opening of the elongated cavity of the one-piece mould and the liquid catheter material would attach to the connector and secure the connector at the distal end of the catheter assembly. Such a method may be advantageous in the case where it is desirable to provide a connector made of a different material, different material characteristics, different colour, etc. than the remaining catheter assembly.

In one embodiment of the present invention the catheter may be a urinary catheter, such as an intermittent urinary catheter.

In one embodiment of the present invention, the liquid catheter material to be injected may be a thermoplastic material. Suitable thermoplastic materials may be materials such as polyurethane, polyvinyl chloride, polyethylene and other thermo-formable materials. The use of thermoplastic materials means that the construction or the shape of the catheter may be partly or fully provided by treating the catheter or the catheter material with heat, such as melting or by solidifying the material by cooling.

BRIEF DESCRIPTION OF THE DRAWINGS

The invention will be explained in greater detail below, describing in example and referring to further advantages of the invention with reference to the drawing, in which.

DETAILED DESCRIPTION OF THE DRAWINGS

Figure 1:
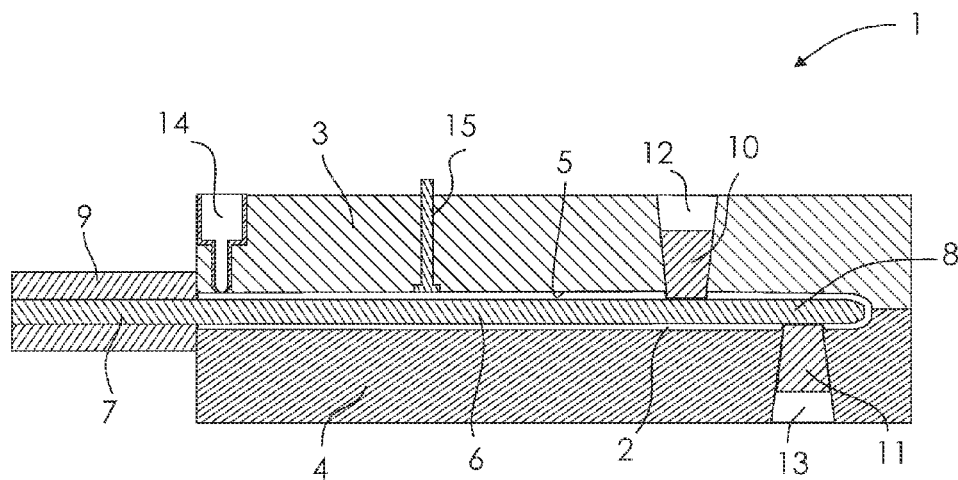
FIG. 1 shows a sectional view of a catheter mould according to the present invention where the mould cavity is provided as two mould halves.

FIG. 1 shows a sectional view of a catheter mould 1 according to the present invention, where a first mould half 3 and a second mould half 4 defines a mould cavity 2 when the first mould half 3 and the second mould half 4 are joined along the longitudinal axis of the mould cavity. During the injection moulding process the mould halves 3,4 are joined so that the surface area 5 of the catheter halves 3,4 defines the external surface of a catheter tube, and subsequent to the injection moulding of the liquid catheter material and upon solidification of the material, the halves 3,4 may be separated to expose the injection moulded catheter assembly. A core pin 6 is provided inside the cavity 2 where the core pin 6 defines the inner lumen of the catheter assembly and the core pin 6 has a distal fixed end 7 and a proximal free end 8. The distal fixed end 7 of the core pin 6 is fixed in place during the injection moulding process, using a fixing apparatus 9 which, upon solidification of the catheter material, allows the core pin 6 to be withdrawn from the cavity 2 and from the inner lumen of the finished catheter tube.

The proximal end 8 of the core pin 6 is stabilized or fixed in its position using a first 10 and a second 11 moulding member which are in physical contact with the core pin 6 during the injection moulding process. The first 10 and the second 11 moulding member may be displaced along a radial axis to the core pin 6, so that during the injection moulding process the moulding members 10,11 are displaced into contact with the core pin 6 so that the moulding members prevent the free end 8 of the core pin 6 from being displaced in a radial direction away from its longitudinal axis. The liquid catheter material used to mould the catheter is injected using an injection sprout 14 which fills up the cavity 2 under high pressure, so that all the volume of the cavity 2 is filled up with liquid catheter material. Subsequent to the solidification of the catheter material, the moulding members 10,11 may be withdrawn from the cavity 2 along their tracks 12,13 so that the first 3 and the second 4 moulding halves may be separated. Upon separation of the first 3 and the second moulding halves 4, the core pin 6 is withdrawn from the moulded material and an ejection pin 15 is used to release the catheter assembly from the first mould half. of the catheter mould 1.

Figure 2:
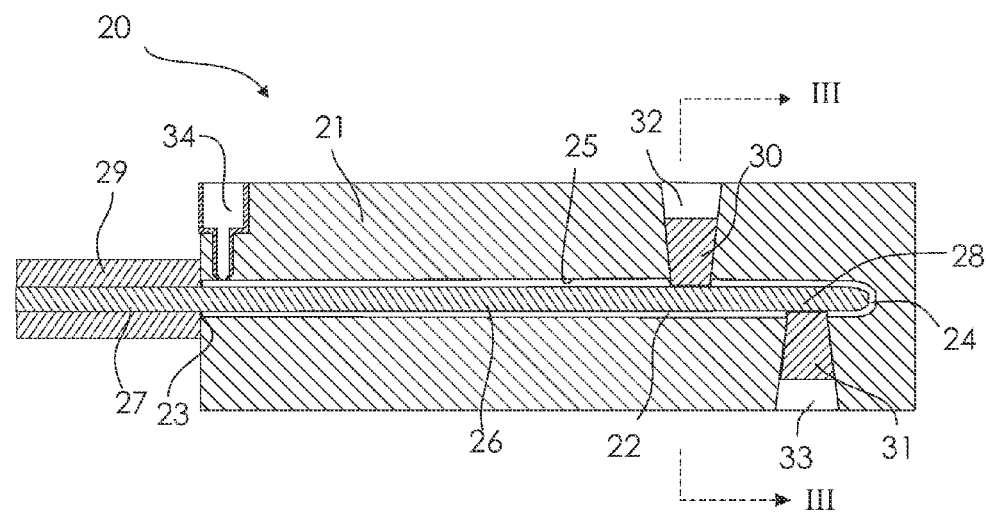
FIG. 2 shows a sectional view of a catheter mould according to the present invention where the mould cavity is provided as an elongated cavity provided in a one-piece mould, FIGS. 3a and b show a sectional view taken along the line III-III in FIG. 2 showing two embodiments of a moulding member supporting a core pin, FIGS. 4a, b and c show a sectional view of a catheter mould where the mould cavity is provided as an elongated cavity provided in a one-piece mould and three steps required for injection moulding of a catheter according to the present invention.

FIG. 2 shows a sectional view of a catheter assembly mould 20 according to the present invention where the mould is made from a single piece of solid material defining a one-piece mould 21. The mould 21 has an elongated cavity 22, having an opening at the distal end 23 of the mould 21 and where the proximal end 24 of the mould 21 defines the catheter tip. The surface area 25 of the cavity 22 defines the outer surface of the catheter assembly to be moulded. During the injection moulding process a core pin 26 is provided inside the cavity 22 where the core pin 26 defines the inner lumen of the catheter assembly to be moulded. The core pin 26 has a distal fixed end 27 and a proximal free end 28. The distal fixed end 27 of the core pin 26 is fixed in place during the injection moulding process, using a fixing apparatus 29 which, upon solidification of the catheter material, allows the core pin 26 to be withdrawn from the cavity 22 and simultaneously withdrawing the moulded catheter tube from the cavity 22. Subsequent to the withdrawal of the core pin 26, the moulded catheter material is removed from the core pin 26.

During the injection moulding process, the proximal free end 28 is stabilized using a first 30 and a second 31 moulding member arranged on tracks 32,33 allowing the moulding members 30, 31 to be radially displaceable inside the cavity. The function and operation of the moulding members 30,31 is similar to the moulding members 10,11 of FIG. 1. The catheter material is injected into the cavity 22 using an injection sprout 34.

Figures 3A, 3B:
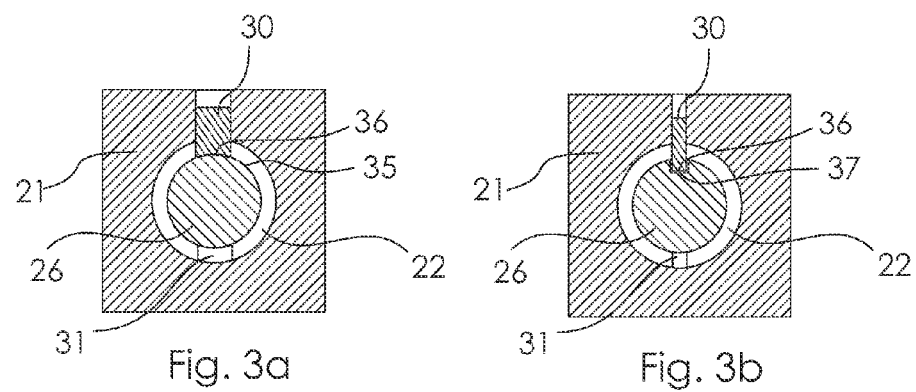

FIG. 3a shows a sectional diagram the mould of FIG. 2 taken along line III-III and shows the one-piece mould 21 having a circular elongated cavity 22. A core pin 26 is positioned inside the cavity 22 in the cavity's substantial centre. The moulding member 30 may be seen having a free end 36 that has a curvature corresponding to the curvature of the external surface 35 of the core pin 26, so that the moulding member embraces the core pin 26 and ensures that the core pin 26 cannot be displaced in a direction towards the moulding member 30 or to the sides, without being displaced in a direction away from the moulding member 30. In order to prevent the core pin from being capable of moving away from the moulding member 30, the opposing moulding member 31 embraces the opposite side of the core pin 26, and together the moulding members 30,31 prevent the core pin 26 from being displaced to the sides.

FIG. 3b shows a similar configuration to that of FIG. 3a, where the difference is that the free end 36 of the moulding member 30 plugs into a depression 37 or a cavity in the core pin 26, and by plugging the moulding member 30 and its opposite moulding member 31 and the core pin 26 together, the core pin 26 is prevented from being displaced in a radial direction of the cavity 22.

As is shown in FIG. 1, 2 and/or FIG. 3, the moulding members may be shaped in such a form that the shape of the moulding members define the drainage eyes of the catheter, as upon removal of the moulding members a through-going opening between the outside surface of the catheter tube and the inner lumen of the catheter tube is provided.

Based on the present disclosure of FIG. 3, it is to be understood that it would be obvious for the skilled person to modify the mould of FIG. 1 to include the same or similar features.

Figure 4A:
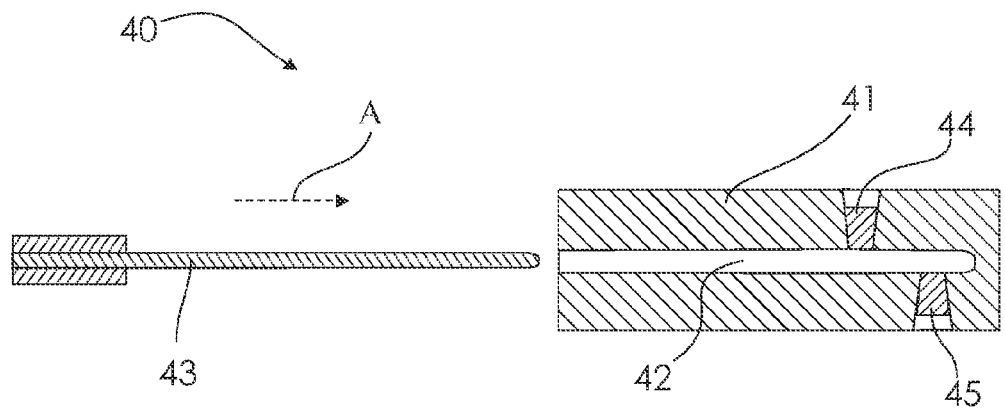

FIG. 4a shows a moulding setup 40 having a one-piece mould 41 with an elongated cavity 42 and a core pin 43 that is positioned outside the elongated cavity 42. The one-piece mould 41 has a first moulding member 44 and a second moulding member 45 which are withdrawn from the cavity 42 when the core pin is positioned outside the cavity. Prior to the injection moulding, the core pin 43 is moved into the cavity 42 in a longitudinal direction, shown by arrow A.

Figure 4B:
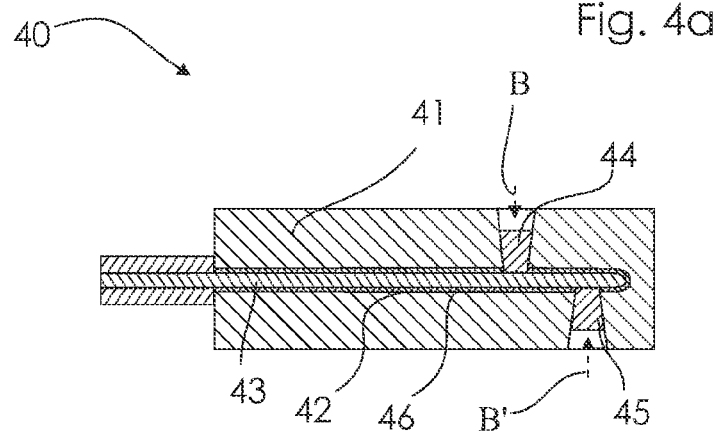

When the core pin 43 has been fully inserted into the cavity 43, as shown in FIG. 4b, the first moulding member 44 and the second moulding 45 member are displaced into contact with the core pin 43 in a radial direction towards the core pin, shown by arrows B and B'. Subsequently, the liquid catheter material is injected into the mould, where the liquid catheter material fills the cavity 42 and surrounds the part of the core pin 43 arranged inside the cavity 42.

Figure 4C:
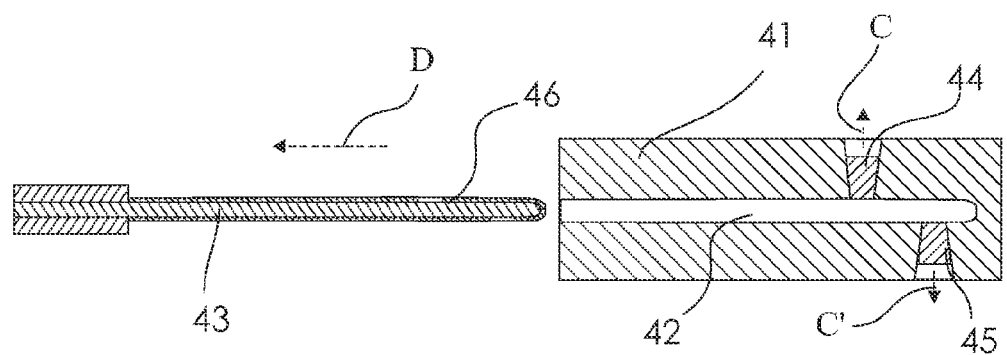

After the catheter material has been injected into the cavity 42, the liquid catheter material solidifies and forms a moulded catheter assembly 46. Subsequent to the solidification, the first moulding member 44 and the second moulding member 45 are displaced in a radial direction away from the core pin 43, shown by the arrow C and C' in FIG. 4c so that the moulding members are withdrawn from the cavity 42. Then, the core pin 43 may be withdrawn from the cavity 42 in a longitudinal direction away from the cavity, show by arrow D, where the moulded catheter assembly 46 is still attached to the core pin 43. Upon the complete withdrawal of the core pin 43 from the cavity 42, the catheter assembly 46 may be removed from the core pin, and the process may start from the top, as shown in FIG. 4*a*.

Figure 5:
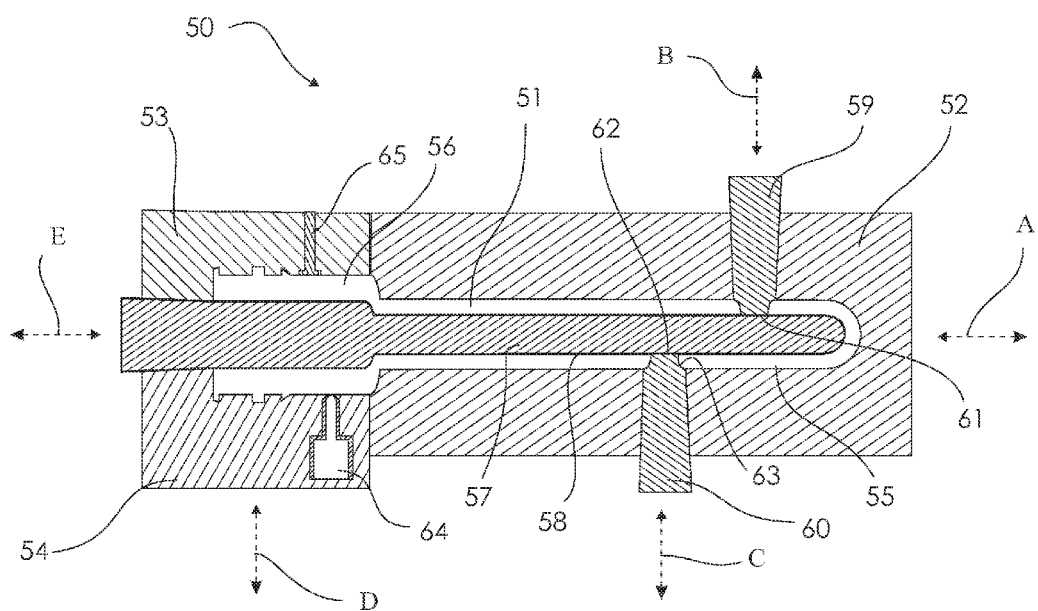
FIG. 5 shows a sectional view of a catheter mould having a one-piece mould for the moulding of the catheter tube and a mould having two halves for injection moulding a connector.

FIG. 5 shows an embodiment of a catheter assembly mould 50 according to the present invention, where the mould 50 defines a cavity 51 and is provided as a one-piece mould 52 defining the cavity 55 for the proximal part end of the catheter assembly and as a mould having a first half 53 and a second half 54 for defining the cavity 56 for the distal end of the catheter assembly. A core pin 57 is provided inside the cavity 51 during the injection moulding process, where the outer surface 58 of the core pin 57 defines the inner surface of the moulded catheter assembly. During the injection moulding, the core pin 57 is supported by a first moulding member 59 and a second moulding member 60, which during injection moulding are arranged inside the cavity of the distal 56 end of the catheter assembly. The free ends 61,62 of the moulding members 59,60 are shaped in the form of rounded drainage eyes. The shape of the sides 63 of the moulding members 59,60 close to its free ends 61, 62 is concave, resulting in a convex shaped outer edge of the drainage eye of the catheter assembly.

During the injection moulding process, the liquid catheter material is injected into the cavity 51 using an injection sprout 64 and the material fills the cavity 51 providing the material for a catheter assembly. Upon solidification of the catheter material, the moulding members 59,60 are withdrawn from the cavity 51, the one-piece mould 52 is displaced away from the catheter assembly, the second half 54 is displaced away from the catheter assembly, the core pin is withdrawn from the catheter assembly and the catheter assembly is left in the stationary first half 53 and subsequently ejected using an ejection pin 65.

The displacement directions of the moveable parts in the mould 50 is shown using the arrows A, B, C, D and E for the one-piece mould 52, the first moulding member 59, the second moulding member 60, the second half 54 and the core pin 57, respectively.

During injection moulding, the parts of the moulds are joined together, while subsequent to the injection moulding, the moveable parts are displaced away from the moulded catheter assembly.

The invention claimed is:

1. A method of injection moulding a catheter assembly comprising a catheter tube having a proximal end and a distal end, an insertable tip closing off the proximal end of the catheter tube and at least two drainage eyes arranged on the side walls of the catheter tube, the method comprising:
providing a proximal single piece mould having an elongated cavity having a longitudinal axis and having a cylindrical shape defining an external surface of the catheter assembly,
providing a core pin inside the cavity in the longitudinal axis of the elongated cavity, where the core pin is in the form of an inner lumen of the catheter assembly where the core pin has a distal end that is fixed in place and a proximal free end,
providing a first and a second moulding member, each one of the first and the second moulding members having a fixed end and a free end, in a radial direction in relation to the longitudinal axis of the elongated cavity,
where the elongated cavity is in the form of the external surface of the catheter tube and the catheter tip, and
distally, a first half and a second half that mate each other longitudinally or vertically and define the mould cavity of a drainage outlet, such as a catheter connector, when assembled and separate longitudinally or vertically to expose the cavity,
preparing the mould by arranging the free ends of the two moulding members to support the core pin,
injecting a liquid catheter material into the mould,
letting the liquid material solidify,
withdrawing the two moulding members from the core pin in a radial direction away from the core pin, and
removing the catheter assembly from the mould.

2. The method according to claim 1, wherein the first and the second moulding members are positioned on opposite sides of the elongated cavity.

3. The method according to claim 1, wherein the first and the second moulding members are positioned in an area that is proximal to approximately 50% of the length of the core pin.

4. The method according to claim 1, wherein the first and the second moulding members are positioned in an area that is proximal to approximately 70% of the length of the core pin.

5. The method according to claim 1, wherein the first moulding member is positioned inside the elongated cavity at a first longitudinal position and the second moulding member is positioned inside the elongated cavity at a second longitudinal position that is different from the first longitudinal position.

6. The method according to claim 1, wherein the first and the second moulding members are provided having a shape that defines drainage eyes arranged in side walls of the catheter tube.

7. The method according to claim 1, wherein the free ends of the two moulding members provided are shaped so that the outer edge of the at least two drainage eyes is rounded during the injection moulding.

8. The method according to claim 1, wherein the outer edge of the at least two drainage eyes is rounded subsequent to the removal of the catheter assembly from the mould.

9. The method according to claim 1, wherein the mould is provided comprising a first half and a second half that mate each other longitudinally or vertically and define the mould cavity when assembled and separate longitudinally or vertically to expose the cavity.

10. The method according to claim 1, wherein the mould provided is a single piece mould having an elongated cavity, where the elongated cavity is in the form of the external surface of the catheter assembly, and the catheter assembly is removed from the mould by a withdrawal along the longitudinal axis of the catheter assembly.

11. The method according to claim 1, wherein the mould provided further comprises a cavity defining a connector where the connector is injection moulded simultaneously with the catheter assembly.

12. The method according to claim 1, wherein a connector is provided in the injection mould prior to the injection moulding of the catheter assembly.

* * * * *